(12) United States Patent
Le Beguec

(10) Patent No.: US 7,112,203 B2
(45) Date of Patent: Sep. 26, 2006

(54) APPARATUS FOR THE PREPARATION OF A FEMUR BONE FOR THE IMPLANTATION OF A PROSTHESIS

(75) Inventor: Pierre Le Beguec, Rennes (FR)

(73) Assignee: Centerpulse Orthopedics Ltd., Baar (CH)

( * ) Notice: Subject to any disclaimer, the term of this patent is extended or adjusted under 35 U.S.C. 154(b) by 154 days.

(21) Appl. No.: 10/443,633

(22) Filed: May 22, 2003

(65) Prior Publication Data

US 2004/0015239 A1    Jan. 22, 2004

(30) Foreign Application Priority Data

May 23, 2002    (FR) .................................. 02 06291

(51) Int. Cl.
*A61B 17/16* (2006.01)

(52) U.S. Cl. ...................................................... 606/85

(58) Field of Classification Search .................. 606/79, 606/80, 84, 85, 86, 89, 95, 102; 623/22.41, 623/22.42, 22.45, 23.18, 23.35, 23.44, 23.45, 623/23.26

See application file for complete search history.

(56) References Cited

U.S. PATENT DOCUMENTS 2,719,522 A * 10/1955 Hudack .................... 623/23.15
3,918,441 A * 11/1975 Getscher ...................... 606/64
4,944,763 A * 7/1990 Willert et al. ............. 623/23.29
4,963,155 A * 10/1990 Lazzeri et al. ............ 623/22.42
5,061,287 A * 10/1991 Feiler ....................... 623/23.48
5,080,685 A * 1/1992 Bolesky et al. .......... 623/22.42
5,089,004 A * 2/1992 Averill et al. ................ 606/85
5,403,320 A * 4/1995 Luman et al. ............... 606/89
5,441,501 A * 8/1995 Kenyon ........................ 606/85
5,484,443 A * 1/1996 Pascarella et al. ............ 606/86
5,766,261 A * 6/1998 Neal et al. ................ 623/21.15
6,117,138 A * 9/2000 Burrows et al. .............. 606/80
6,126,694 A * 10/2000 Gray, Jr. ................... 623/22.11

* cited by examiner

*Primary Examiner*—Eduardo C. Robert
*Assistant Examiner*—David Comstock
(74) *Attorney, Agent, or Firm*—Christie, Parker & Hale, LLP

(57) ABSTRACT

An apparatus for the preparation of a cement-free implantation of a prosthesis is provided. The prosthesis has a distal part corresponding to a diaphysial region of the femur, a proximal part corresponding to a metaphysial region of the femur, and an intermediate region which corresponds to a metaphysial-diaphysial region. The apparatus includes a rasp of modular design including a conical distal part and first and second proximal parts of substantially different basic shapes and heights. The apparatus also includes a releasable connection means at the distal part for connecting a proximal part to at least one distal part. The apparatus also includes a neutral intermediate element mountable on the distal part of the rasp for driving it and for measuring its degree of recessing on a graduated scale.

8 Claims, 2 Drawing Sheets

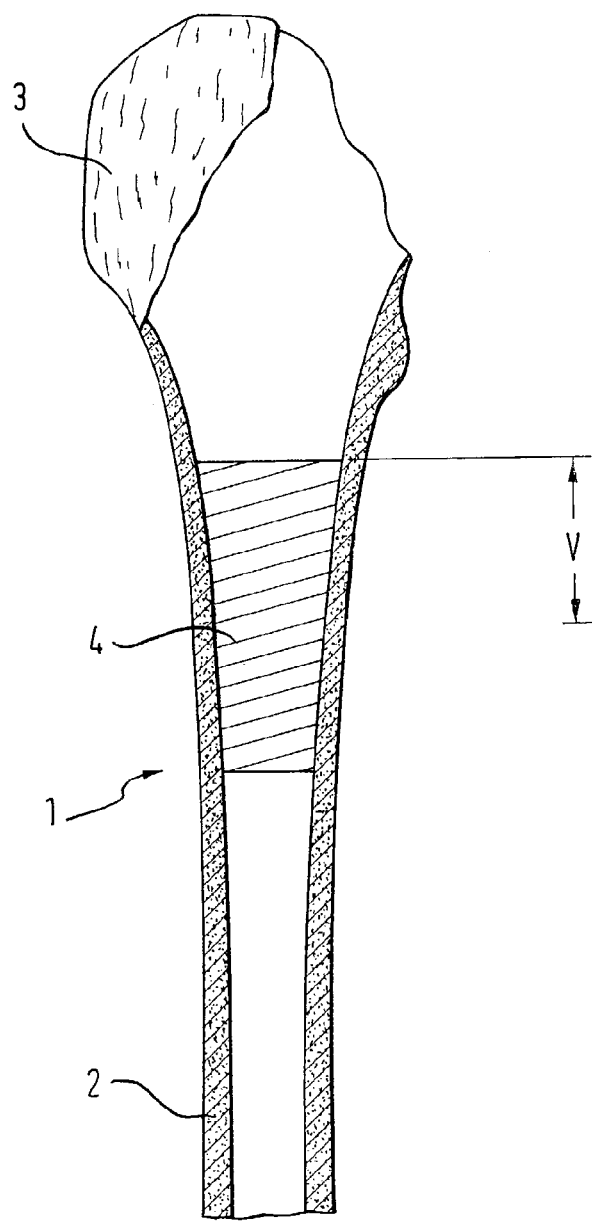
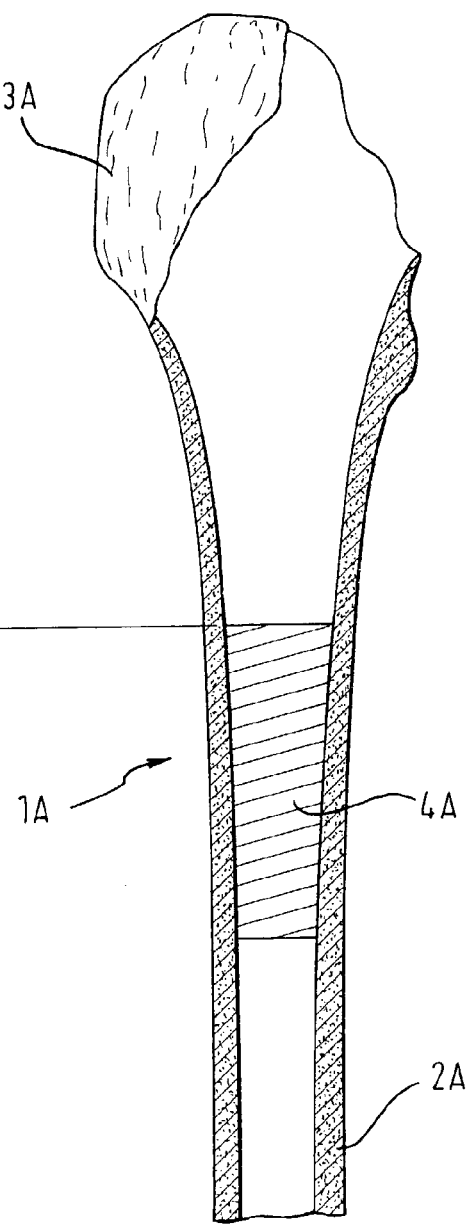

Fig. 3
Fig. 4
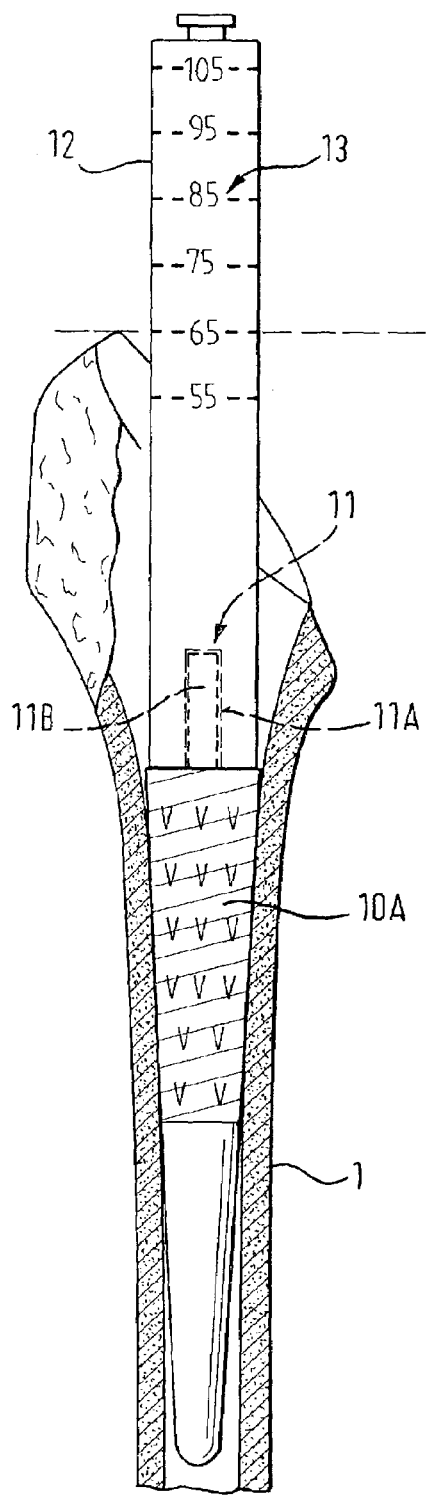
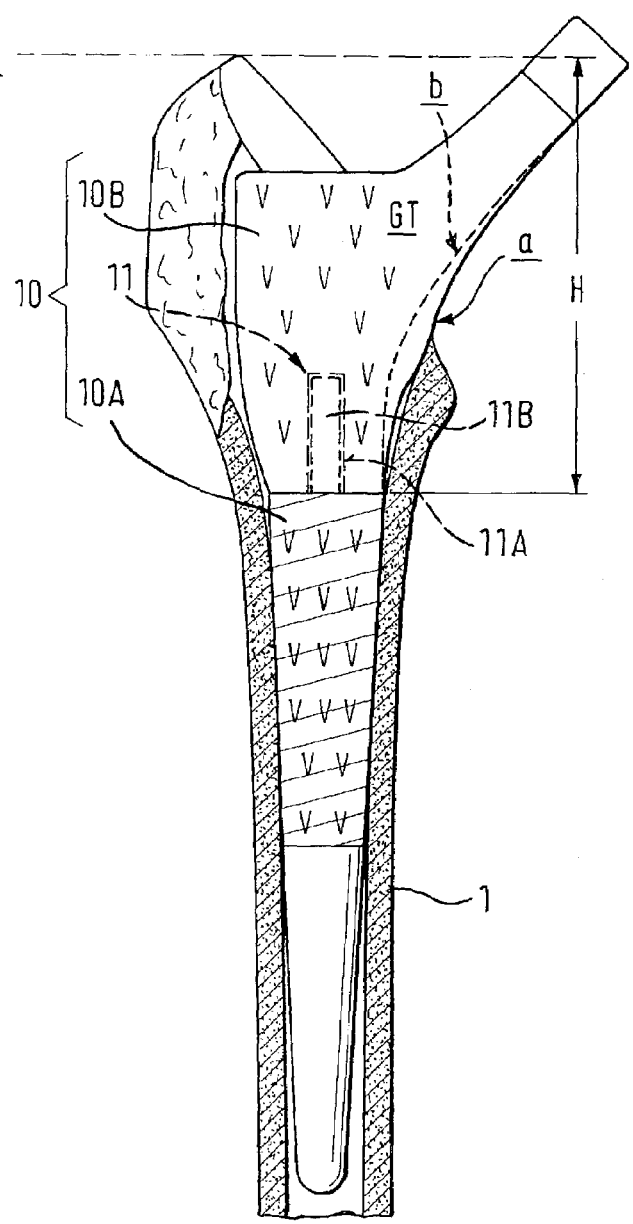

APPARATUS FOR THE PREPARATION OF A FEMUR BONE FOR THE IMPLANTATION OF A PROSTHESIS

CROSS-REFERENCE TO RELATED APPLICATION

This application claims priority of France Patent Application No. 02 06291, filed on May 23, 2002.

The invention relates to the preparation of a femur bone for the purpose of the cement-free implantation of a prosthesis with so-called press-fit-effect.

In the area of hip joint prosthesis two large groups of cement-free femur shafts are known, which are intended to be implanted into a femur bone with the aid of a reamer or a rasp.

There are, on the one hand, so-called first implantation femur prostheses which are used on the patient for the first time and, on the other hand, other so-called revision prostheses which, as the name already says, are able to replace an implant which has failed.

In both cases the main aim is to ensure a complete primary stability of the femur shaft or implant.

In order to achieve this object, i.e. a firm mechanical connection between the prosthesis and the surrounding bone, several methods exist of which two are frequently used and indeed the use of a locking shaft and the already mentioned so-called press-fit concept.

In order for the press-fit concept to be effective two important conditions must be satisfied simultaneously and indeed the generation of a contact surface between the bone and the implant and a problem-free wedging of the prosthesis in this contact region.

In order to achieve both these goals, a careful preparation of the medullary space of the femur or femur bone must be effected, which is always difficult, in particular when a prosthesis is involved. This is a consequence of the anatomical fluctuations and/or of the loss of bone substance which can occur.

The object underlying the present invention thus lies in determining in advance and with precision the region of the femur in which one can carry out the press-fit, bearing in mind that in all cases the equality in length of the two lower limbs of the patient must be maintained and, so far as possible, restricting the region of contact between the bone and the implant to the proximal part of the femur, in order not to overstiffen the entire femur.

Another difficulty results when the so-called press-fit region is disposed at different levels in the femur bone.

It is namely relatively rare for this press-fit region to lie in the upper metaphysial region, i.e. above the small trochanter, since at this level numerous anatomic fluctuations arise when a first implantation is involved and bone substance losses arise when concerned with an exchange of the prosthesis.

The region of the femur which can be used most reliably and best of all mainly lies in the middle part of the femur, i.e. in the metaphysial-diaphysial region, i.e. at the level of and below the small trochanter, in the zone which is disposed above the diaphysial region, where too much pressing fixation should be avoided.

This ideal region for the carrying out of the press-fit can thus vary with respect to the height of the prosthesis depending on the morpho-type and the degree of bone damage of the patient involved.

In order to satisfy this above object and take account of the physical difference from patient to patient, there is provided an apparatus for the preparation of a femur bone for the cement-free implantation of a prosthesis having a so-called press-fit-effect, the prosthesis having a distal part corresponding to a diaphysial region of the femur, a proximal part corresponding to a metaphysial region of the femur and an intermediate region in which the press-fit-effect is preferably provided and which corresponds to a metaphysial-diaphysial region, with the height of the prosthesis being variable depending on the morpho-type and degree of bone damage, characterized in that the apparatus consists of a modulatable rasp including a plurality of parts, at least one of which has a conical distal part of a single size and of a single shape, there being at least first and second proximal parts of substantially different basic shapes, each of said first and second proximal parts being provided in a plurality of increasing heights, there being releasable connection means at said distal part for connecting a proximal part selected in dependence on the morpho-type and on the degree of recessing of the distal part to said at least one distal part, and also a neutral intermediate element forming a proximal gauge, said neutral intermediate element being mountable on said distal part of the rasp for driving it and for measuring its degree of recessing on a graduated scale, which establishes both the correct length of the prosthesis to be inserted and the size of the required proximal part of the rasp necessary for the preparation of the femur bone to receive the said prosthesis.

The apparatus of the invention thus provides a modular system for the preparation of the femur which permits a graduated preparation of the femur. This means that, in a first step, the press-fit range, termed the primary stability range, has to be found and prepared and that, in a second step, the femur has to be prepared in its proximal region in order to select the femur shaft which is best suited to re-establish the correct length for its lower prosthetic part.

An apparatus of this kind in accordance with the invention has decisive advantages and indeed:

on the one hand, a good preparation of the selected region is ensured in which the primary stability is to take place in the metaphysial-diaphysial region, and indeed with the distal part of the rasp. The intermediate element or gauge has in fact no preparatory action on the femur, it only serves to measure the desirable size of the proximal rasp, on the other hand, a blockage at three points (in the proximal metaphysial region) is avoided. Such a blockage would give rise to the danger that secondary sinkage could arise with an inadequate stability against rotation. This is always possible with a conventional rasp made in one piece and should definitely be avoided, since this is no longer a press-fit effect but rather a simple insecure blockage.

The present invention also relates to the features which result from the following description and which are to be considered individually or in all their possible technical combinations.

In the description a non-limiting example will be described, with reference to the accompanying drawing showing how the invention can be executed. In this drawing is now shown:

FIGS. 1 and 2 sections through femur bones of different morpho-types with press-fit regions which likewise have different heights, FIG. 3 a section through a femur bone in accordance with one of the FIGS. 1 and 2 in which a first form of the preparation apparatus is being used in accordance with a first phase, FIG. 4 a section through a femur bone in accordance with one of the FIGS. 1 and 2 in which a second form of a composite preparatory apparatus is being used in accordance with a second phase which follows the first phase of FIG. 3.

As shown by FIGS. 1 and 2 a femur bone 1 or 1A has a distal part 2, 2A corresponding to a diaphysial region of the femur 1, 1A, a proximal part 3, 3A corresponding to a metaphysial region of the femur 1, 1A and an intermediate region 4, 4A in which the press-fit effect is preferably obtained and which corresponds to a metaphysial-diaphysial region, the depth of which (i.e. the distance measured from the apex of the large trochanter to the upper end of the intermediate region) differs depending on the morpho-type and the degree of bone damage.

As can be seen in the FIGS. 1 and 2 the difference in depth of the metaphysial-diaphysial regions in which the press-fit effect is obtained vary by a value "V".

Precisely this difference in values must be controlled, depending on the aim that is to be achieved, in order to obtain not only the press-fit effect, and thus a good primary stability, but rather also a correct preparation of the metaphysial proximal region of the femur. The control and the correct preparation must be effected in dependence on the position and shape of the femur proximally of the named press-fit region, to ensure the correct mounting of a prosthesis corresponding to the shape of the femur (morpho-type) and so that the height of the prosthesis permits the maintenance of a correct length of the lower prosthetic part, the primary stability of which, when inserted in the bone, should be obtained in the metaphysial-diaphysial region and not in the proximal metaphysial region.

The means for specifically carrying out the invention consist on the one hand of a modulatable rasp 10 consisting of several parts or modules. One of these parts is a starkly conical distal part 10A of a single size and of a single shape. However, more than one size and shape could be used if desired. Furthermore, there are provided a plurality of proximal parts 10B. These proximal parts have at least two different basic shapes and each basic shape comes in a plurality of increasing heights. The proximal part, which is specifically selected in dependence on the morpho-type and on the degree of countersinking of the distal part, can be firmly connected to the distal part 10A by releasable connection means 11. The compositions or modules of the modulatable rasp also include a neutral intermediate element 12, which forms a proximal gauge and which is first attached to the distal part 10A of the rasp 10, e.g. using the same releasable connection means 11 (FIG. 3), serves for the measurement of the recessed position of the distal part 10A at a graduated scale 13 provided on the neutral intermediate element 12. This scale 13 shows the correct length of the femur to be remanufactured and thus the size of the proximal part 10B of the rasp which is to be selected and arranged at the location of and in place of the intermediate element and gauge 12 for the preparation of this femur bone 1 or 1a.

As FIG. 3 shows the intermediate element and gauge 12 is of cylindrical shape with a diameter which is somewhat smaller than the maximum diameter of the distal part 10A of the rasp.

In accordance with the present non-limiting example the intermediate element and the gauge 12 has a scale 13 of six different heights which corresponds to six proximal parts 10B of the rasp 10.

In accordance with a preferred embodiment, which is shown in FIG. 4, the proximal parts 10B of the rasp 10 are of two different shapes and each shape is present with heights H increasing in 10 mm steps from 55 mm to 105 mm. In this connection the first shape "a" is the standard shape whereas the second possible shape "b", which is illustrated by a broken line towards medial, is for a longer distance cylindrical in shape before it turns in the direction of the neck.

In this manner the distal part 10A of the rasp 10 has a length of 120 mm and a minimum diameter at the distal end of 12 mm, it could however also have a different length and a different diameter.

In accordance with another feature of the invention the means 11 for the connection of the proximal part 10B of the rasp to its distal part 10A is the same as that for the connection of the same distal part 10A of the rasp 10 and of the intermediate element and gauge 12, which can previously be mounted on the same.

In accordance with the present embodiment the connection means 11 consist of a mounting part 11A which forms a flattened axial recess 11A, which is formed at the end of the proximal part 10B of the rasp 10 or at the end of the intermediate element and gauge 12. The flattened axial recess can, e.g., have a cross-section resembling the shape of a circle flattened at one side (D-shape) or the shape of a circle flattened at two opposite sides. The flattened axial recess drivingly cooperates with a corresponding part 11B which is formed at the end of the distal part 10A of the rasp and which is inserted into the flattened axial recess 11A, or vice versa. The inserted part 11B and the flattened axial recess 11A are designed to cooperate to achieve a predetermined clamping effect by which the relative clearance between the parts can be suppressed.

In accordance with a non-illustrated variant the connection means consist of a threaded bore which is formed at the end of a proximal part 10B of the rasp or at the end of the intermediate element and gauge 12 and which can drivingly cooperate with a corresponding threaded part, which is arranged at the end of the distal part 10A of the rasp, or vice versa, in order to obtain a clearance-free connection.

The intermediate element 12 serves exclusively to push distal part 10A of the modulatable rasp 10 and to measure the distance H from the distal part 10A to the apex of the great trochanter (centre of rotation CR), in order to permit the selection of the correct proximal part 10B of the rasp necessary to re-establish the correct length of the lower prosthetic part during the mounting of the prosthesis.

The manner of proceeding with this apparatus is as follows:
  sectioning of the femur neck, if one is concerned with a prosthesis for a first implantation, or removal of the loosened implant and of the entire cement, if one is concerned with an exchange,
  lateral opening of the large trochanter,
  mounting of the single distal part 10A of the rasp 10 onto the intermediate element and gauge 12 via the connection means 11,
  driving this unit into the femur bone 1 or 1A until a problem-free primary stability of a distal rasp on which the gauge is mounted is obtained, which permits the effective determination of the stability of the assembly,
  reading off the scale division 13 on the scale of the intermediate element and gauge 12 for determination of the degree of the recessing or counter-sinking which corresponds to the centre of rotation CR of the proximal part 10B which is to be selected and which coincides with the apex of the large trochanter GT, selection of the proximal part 10B of the rasp in dependence on the morpho-type and on the height which corresponds to the preceding read-off at the intermediate element and gauge 12, firm connection of the distal part 10A with the selected proximal part 10B. If the latter is not suitable and can not be countersunk sufficiently far then it indicates to the surgeon that he must carve out the femur in its proximal part in order to be certain that the blocking remains distal, boring out of the proximal metaphysial part of the femur.

Thereafter the rasp consisting of the distal part 10A and the appropriate proximal part 10B is removed and the appropriate prosthesis is fitted.

It is to be emphasized that the unit comprising the distal part 10A and the proximal part 10B must be countersunk or recessed over a correct height H, i.e. the later centre of rotation (CR) of the proximal part of the rasp 10B and of the prosthesis must correspond to the apex of the trochanter (GT) in order to be certain that a good contact exists in the metaphysial-diaphysial zone between the bone and the implanted prosthesis.

If this is not the case, then a supplementary preparation (carving out) must be carried out of only the proximal metaphysial region of the femur.

The clinical tests have shown that the apparatus of the invention, which is used in accordance with the above-described working technique, enables a good press-fit action in the region provided for this, i.e. in the metaphysial-diaphysial region and simultaneously leads to the re-establishing of the correct length of the lower prosthetic part.

The invention claimed is:

1. Apparatus for the preparation of a femur bone for the cement-free implantation of a prosthesis having a press-fit-effect, the prosthesis having a distal part corresponding to a diaphysial region of the femur, a proximal part corresponding to a metaphysial region of the femur and an intermediate region in which the press-fit-effect is provided and which corresponds to a metaphysial-diaphysial region, with the height of the prosthesis being variable depending on the morpho-type and degree of bone damage, the apparatus comprising a rasp of modular design including a plurality of parts, at least one of which has a conical distal rasp part of a single size and of a single shape, there being at least first and second proximal rasp parts of substantially different basic shapes, each of said first and second proximal rasp parts being provided in a plurality of increasing heights, there being releasable connection means at said distal rasp part for connecting both of the proximal rasp parts, one of which being selected in dependence on the morpho-type and on the degree of recessing of the distal rasp part, to said at least one distal rasp part, and also a neutral intermediate element forming a proximal gauge, said neutral intermediate element also being connectable on said distal part of the rasp for driving it and for measuring its degree of recessing on a graduated scale which is adapted to the plurality of increasing heights of the proximal rasp parts and which establishes both the correct length of the prosthesis to be inserted and the size of the required proximal part of the rasp necessary for the preparation of the femur bone to receive the prosthesis to be inserted.

2. Apparatus in accordance with claim 1, wherein said intermediate element is also provided with complementary connections means for connection to said connections means of said distal part.

3. Apparatus in accordance with claim 1, wherein the intermediate element is of cylindrical shape and has a diameter somewhat smaller than a maximum diameter of said conical distal part of said rasp.

4. Apparatus in accordance with claim 1, wherein the intermediate element has a scale of six different heights which correspond to six proximal parts of the rasp.

5. Apparatus in accordance with claim 1, wherein the proximal parts of the rasp are provided in at least two basic different shapes and each is of increasing height which takes place in 10 mm steps from 55 mm to 105 mm.

6. Apparatus in accordance with claim 1, wherein the conical distal part of the rasp has a length of 120 mm and a smallest diameter of 12 mm.

7. Apparatus in accordance with claim 1, wherein the connection means consists of a receiving part which forms an axially flattened cut-out and is formed at the end of the proximal part of the rasp, or at the end of the intermediate element and can cooperate in driving manner with a corresponding insertion part which is formed at an end of the distal part of the rasp, or vice versa, and in a predetermined clamped arrangement by which the relative clearance between the parts is eliminated.

8. Apparatus in accordance with claim 1, wherein the connection means consist of a threaded bore which is formed at one end of the proximal part of the rasp, or at the end of the intermediate element, and which can cooperate in driving manner with a corresponding part provided with a thread which, is provided at an end of the distal part of the rasp, or vice versa, in order to produce a clearance-free connection.

* * * * *